United States Patent [19]

McRae

[11] Plant 4,174

[45] Jan. 3, 1978

[54] LILY PLANT: LILIUM 'HEADLIGHT'

[75] Inventor: Edward A. McRae, Boring, Oreg.

[73] Assignee: Melridge, Inc., Gresham, Oreg.

[21] Appl. No.: 761,224

[22] Filed: Jan. 21, 1977

[51] Int. Cl.[2] ..... A01H 5/00
[52] U.S. Cl. ..... Plt./68
[58] Field of Search ..... Plt./68

*Primary Examiner*—Robert E. Bagwill
*Attorney, Agent, or Firm*—Eugene D. Farley

[57] ABSTRACT

A new variety of Asiatic hybrid lily plant bearing large clusters of medium-sized flowers of excellent form, strong color, and long persistence, both on the plant and as cut flowers. The plant is characterized by having dark stems and excellent foliage. The flower form is excellent, the petals being broad and of fine substance. The buds display a rich reddish-orange color prior to opening. The flowers are characterized by a rich golden orange color and conspicuous spotting.

1 Drawing Figure

BACKGROUND OF THE INVENTION

My new variety of lily plant originated as a seedling selected from a group of seedlings at Gresham, Oreg. The seedlings were planted during a breeding program carried on by me since the year 1965. This program had as its objective the production of upright Asiatic lilies in the orange color range which had a high tolerance to virus infection, reliability and rapidity of forcing performance, and a flower form superior to Lilium 'Harmony'.

I achieved the desired objective by using as the seed parent Lilium 'Harmony' and as the pollen parent Lilium 'Sunspot'.

My new lily plant is characterized by having single dark stems of medium height and abundant foliage of a deep green color. The buds have a deep reddish-orange color which is shown prior to opening, a characteristic of special valve when the plant is used for cut flowers or as a pot plant forced out of season.

The flower form is excellent, the petals being broad and of fine substance. The color of the flowers is a vivid golden orange which persists over a long period of time both on the plant and on the cut flowers.

My new variety of lily has improved qualities of vigor, disease resistance, and tolerance to infection by virus. It is a rapid natural propagator. It also is an excellent garden plant and is suitable for the production of cut flowers and pot plants by forcing precooled bulbs, all as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows in full color the foliage, the buds, the petal arrangement, the conspicuous maculation, and in particular the intense golden orange color of the flowers.

DESCRIPTION OF THE NEW VARIETY

The following is a detailed description of my new variety of Asiatic hybrid lily, with nomenclature according to *The International Lily Register* (Royal Horticultural Society, London, 2nd edition, 1969), and with color designations according to the Royal Horticultural Society Color Chart, published by the Royal Horticultural Society in 1966.

THE PLANT

Origin: Seedling.
Parentage:
- *Seed parent.*—Lilium X 'Harmony' (unpatented).
- *Pollen parent.*—Lilium X 'Sunspot' (unpatented).

Classification:
- *Botanic.*—Hybrid Lilium cultivar; Division I-B of the Horticultural Classification of Lilies of the R.H.S.
- *Commercial.*—Asiatic hybrid lily.

Form: Single stem, erect and stately.
Height: 25 to 30 inches, from bulbs 5 to 7 inches in circumference.
Growth: Vigorous, sturdy and upright.
Branching: None.
Strength: Excellent.
Foliage:
- *Quantity.*—Abundant.
- *Size of leaf.*—3 inches long.
- *Shape of leaf.*—Lanceolate.
- *Texture.*—Glossy.
- *Color.*—Upper and under sides, both dark green. "Black" stem produced by red pigment over green stem.

Bulbs:
- *Size.*—Any size, ranging up to 12 inches in circumference.
- *Color.*—Pure White.

THE BUD

Form: Obtuse, urn-shaped and long.
Size: About 2 to 3 inches long and about 2 inches in circumference at maturity.
Opening: Bud opens slowly.
Color: Deepest reddish orange when outer tepals first divide and deep golden orange when tepals begin to unfurl.
Tepals: Curled back; golden orange on the inside and deep reddish orange on the outside.
Peduncle: About 2 inches long. Erect and deep green in color.

THE FLOWER

Blooming habit: Annually in early summer; blooms once and profusely.

Size: Medium; 5 to 6 inches in diameter.

Borne: In clusters, from 5 to 12 on a single stem from a bulb 5 to 7 inches in diameter.

Shape: Flat, without substantial change in form with age.

Tepalage:

*Number of tepals.*—6. Very broad (inner tepals 1½ inches wide) and overlapping.

*Arrangement.*—Imbricated.

*Color.*—Golden orange R.H.S. C.C.24A (R.H.S. C.C.24B under low-light conditions) on both the outer and inside portions of the tepal, with the reverse side being a deeper orange. Color deepens slightly as flowers age. White star formed in center of flowers by pubescence along margins of nectaries.

*Tepal longevity.*—Tepals stay on stem about 3 weeks.

*Spots.*—Copious, large, magenta spots, which, in a typical case form a circle 4 inches wide within the flower center.

Pedicel:

*Length.*—About 2 inches.

*Color.*—Deep green.

*Form.*—Pedicel is sturdy and upright.

Color change: Flower color changes to a slightly richer color after full bloom.

Appearance: The flower is satiny.

Disease resistance: The plant and flower are resistant to disease; in particular, they are resistant to Fusarium and Botrytis.

Fragrance: The flower is not fragrant.

Lasting quality: The flowers are very long lasting both on the plant and as cut flowers.

THE REPRODUCTIVE ORGANS

Stamens, anthers:

*Arrangement.*—Typical of Liliaceae.

*Length.*—About 2 inches.

*Number.*—6.

*Filaments.*—2 inches in length; color, reddish orange.

Pollen and anthers: Bright rusty brown in color.

Pistils: One in number with a length of about 2 inches.

Stigma: Deepest purple maroon in color.

Characteristics of ovaries: Typical of genus Lilium.

FRUIT

Fertility: The fruit is fertile.

Shape: The fruit is ovoid in shape.

Color at maturity: The fruit is soft brown at maturity.

My new lily most closely resembles Lilium cultivar 'Harmony', but is distinguishable therefrom by its superior height and flower form, and the intense golden orange color of its flowers. I claim:

1. A new and distinctive variety of Asiatic hybrid lily plant substantially as herein shown and described, characterized by its single stem of dark green color, its abundant lanceolate deep green foliage, the deep reddish orange color of its buds upon first division, and their deep golden orange color upon unfurling, the excellence of its flower form, the exceptional breadth and fine substance of the tepals, the rich golden orange color of the tepals when the flower is in bloom, the resistance of the plant and flower to disease and its tolerance to infection by virus, and the versatility of the plant both as a garden plant and a plant rapidly produced from precooled bulbs forced for cut flowers or pot plants.

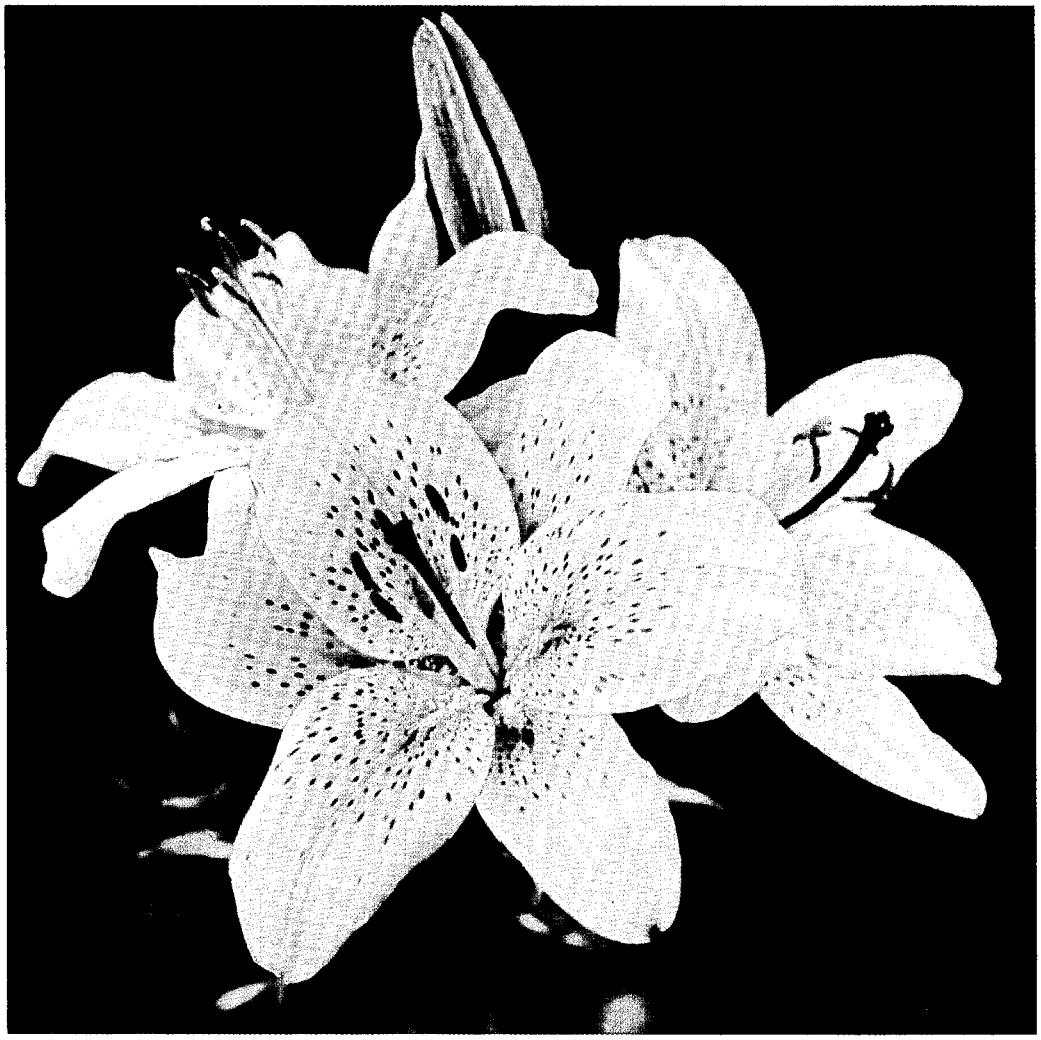

* * * * *